US006149909A

United States Patent [19]

Scott et al.

[11] Patent Number: 6,149,909

[45] Date of Patent: Nov. 21, 2000

[54] SYNTHETIC α-L-IDURONIDASE AND GENETIC SEQUENCES ENCODING SAME

[75] Inventors: Hamish Steele Scott, Millswood; Donald Stewart Anson, Thebarton; Annette Marie Orsborn, Hallett Cove; Paul Victor Nelson, Colonel Light Gradens; Peter Roy Clements, West Lakes; Charles Phillip Morris, Unley; John Joseph Hopwood, Stonyfell, all of Australia

[73] Assignee: Women's and Children's Hospital, Australia

[21] Appl. No.: 09/191,171

[22] Filed: Nov. 13, 1998

Related U.S. Application Data

[62] Continuation of application No. 08/494,104, Jun. 23, 1995, abandoned, which is a continuation of application No. 08/084,254, filed as application No. PCT/AU92/00611, Nov. 12, 1992, abandoned.

[51] Int. Cl.$^7$ .............................. A61K 38/47; C12N 9/24

[52] U.S. Cl. ......................................... 424/94.61; 435/200

[58] Field of Search .......................... 435/200; 424/94.61

[56] References Cited

U.S. PATENT DOCUMENTS

| | | | |
|---|---|---|---|
| 5,422,244 | 6/1995 | Johnson-Wood et al. | 435/7.1 |
| 5,433,946 | 7/1995 | Allen, Jr. et al. | 424/94.3 |

OTHER PUBLICATIONS

Schuchman et al., "Human alpa–L–Iduronidase," J. Biol. Chem., vol. 259, No. 5, pp. 3132–3140, Mar. 10, 1984.

Clements et al., "Immunopurification and characterization of human alpha–L–iduronidase with the use of monolclonal antibodies," Biochem J., (1989) 259, 199–208.

Unger et al., "Recombinant alpha–L–iduronidase: characterization of the purified enzyme and correction of mucopolysaccharidosis type I fibroblasts," Biochem. J. (1994) 304, 43–49.

Anson et al. (1992) "Correction of Mucopolysaccharidosis Type I Fibroblasts by Retroviral–Mediated Transfer of the Human α–L–Iduronidase Gene", *Human Gene Therapy*3:371–379.

Brooks et al. (1992) "Hurler Syndrome: A Patient with Abnormally High Levels of α–L–Iduronidase Protein", *Biochemical Medicine and Metabolic Biology*47: 211–220.

Clements et al. (1985) "Human α–L–Iduronidase", *Eur. J. Biochem.*152:21–28.

Fujibayashi et al. (1984) "Properties of α–L–Iduronidase in Cultured Skin Fibroblasts from α–L–Iduronidase–Deficient Patients", *Human Genetics*65(3):268–277.

Herd et al. (1976) "In Vitro Correction of Hurler Fibroblasts with Bovine Testicular Hyaluronidase", *Proceedings of the Society for Experimental Biology and Medicine*151:642–649.

Herd et al. (1985) "Purification of α–L–Iduronidase from Human Seminal Plasma", *Experimental Biology*:8059.

Moskowitz et al. (1992) "Cloning and Expressing of cDNA Encoding the Human Lysosomal Enzyme, α–L–Iduronidase", *FASEB Journal*6:A77.

Ohshita et al. (1989) "Purification, Characterization and Subcellular Localization of Pig Liver α–L–Iduronidase", *Eur. J. Biochem.*179:201–207.

Rome (1982) "α–L–Iduronidase from Human Kidney", *Methods in Enzymology*83:578–582.

Schuchman et al. (1984) "Regional Assignment of the Structural Gene for Human α–L–Iduronidase", *Proc. Natl. Acad. Sci. USA*81:1169–1173.

Scott et al. (1991) "Human α–L–Iduronidase:cDNA Isolation and Expression", *Proc. Natl. Acad. Sci. USA*88:9695–9699.

Scott et al. (1992) "Structure and Sequence of the Human α–L–Iduronidase Gene", *Genomisc*13:1311–1313.

Stoltzfus et al. (1992) "Cloning and Characterization of cDNA Encoding Canine α–L–Iduronidase", *The Journal of Biological Chemistry*267(10):6570–6575.

Myerowitz, R., et al. (1981) "Maturation of α–L–Iduronidase in Cultured Human Fibroblasts", *The Journal of Biological Chemistry*, 256(6):3044–3048.

*Primary Examiner*—Robert A. Wax
*Attorney, Agent, or Firm*—Ann R. Pokalsky

[57] ABSTRACT

The present invention relates generally to α-L-iduronidase and to genetic sequences encoding same. More particularly, the present invention provides an isolated nucleic acid molecule comprising a sequence of nucleotides which encodes or are complementary to a sequence which encodes a mammalian α-L-iduronidase or fragment or derivative thereof and to the recombinant enzyme encoded thereby. These molecules are useful in the investigation, diagnosis and treatment of subjects suspected of or suffering from α-L-iduronidase deficiency.

11 Claims, 9 Drawing Sheets

Figure 2c

B——————————————————————————B peptide 5'

R S V A V T L R L R G V P P G P G L V Y V T R Y L D H G L C S P D G E W R R L G 491
CCGCAGCGTCGCGGTGACCCTGCGGCTGCGCGGGGTGCCCCCCGGCCCCGGCCTGGTCTACGTCACGCGCTACCTGGACAACGGGCTCTGCAGCCCCGACGGCGAGTGGCGGCGCCTGGG 1560

R P V F P T A E Q F R I M R A A E D P V A A A P R P L P A G G R L T L R P A L R 531
CCGCCCCGTCTTCCCCACGGCAGAGCAGTTCCCCCCCATGCCCCCCCCTCACCACCCCCTCCCCCCCCCCCCCCCCCCTTACCCCCCCCCCCCCGCCTGACCCTCCCCCCCCCGCTGGG 1680 peptide 1

L P S L L L V H V C A R P E K P P G Q V T R L R A L P L T Q G Q L V L V W S D E 571
GCTGCCGTCGCTTTTGCTGGTGCACGTGTGTGCGCGCCCCGAGAAGCCCGCCCGGGCAGGTCACGCGGCTCCCCGCCCTGCCCCTGACCCAACCCCAGCTGTTCTGGTCTGGTCCCATGA 1800 peptide 1'

H V G S K C L W T Y E I Q F S Q Q G K A Y T P V S R K P S T F H L F V F S P D T 611
ACACGTGGGCTCCAAGTGCCTGTGGACATACGACATCCAGTTCTCTCAGGACCCTAAGGCGTACACCCCGGTCAGCAGGAAGCCATCGACCTTCAACCTCTTTGTGTTCAGCCCAGACAC 1920 peptide 7 peptide 5

G A V S G S Y R V R A L D Y W A R/ P G P F S D P V P T L E V P V P R G P P S P G 651
AGGTGCTGTCTCTGGCTCCTACCGAGTTCGAGCCCTGGACTACTGGGCCCGACCAGGCCCCTTCTCGGACCCTGTGCCGTACCTGGAGGTCCCTGTGCCAAGAGGGCCCCCATCCCCCCC 2040

H P 633
CAATCCATGAGCCTGTGCTGAGCCCCAGTGGGTTGCACCTCCACCGCCACTCAGCCAGCTCCCCCTGCACTGTGCCCATGCTGCCCTCCCATCACCCCCTTTGCAATATATTTTT 2155

```
ttaaatatgtatattcgtattgctttggcttaaacaatatttcagtcctgccttggttgaatccatggatctgaagccaagtgtaaggagggcccagtgtgctcttctggggtaattctc 120
cttcctgctaaagcgcacgctttactcaggaggctggggtgagaaaatcgctgaagccccggagatggaggttgcagtgagctgagatcgcgccactgcacctcagcctgggcgacaaag 240
caagactctgtctcaaaaacacacaaaaacagagaaaaacaagacagtaatggctcaactcacatagcaccaacgggcgaagcgttcttctgagcgctttccgagtcatcggtcctcaga 360
gcagcccctgaggcccgcaaggaagcggggctccaagccctgccgtgctcccggctccccgaggctccccgaggccacccaacccctcccacccggccatcgcccccctcaccaaggcccc 480
gccccggcgcggcggtcacatggggtgcgcgcccagactccgacccggaggcggaaccggcagtgcagcccgaagccccgcagtccccgagcacgcgtggccATGCGTCCCCTGCGCCCC 600
CGCGCCGCGCTGCTGGCGCTCCTGGCCTCGCTCCTGGCCGCGCCCCCGGTGGCCCCGGCCGAGGCCCCGCACCTGGTGCAGGTGGACGCGGCCCGCGCGCTGTGGCCCCTGCGGCGCTTC 720
TGGAGGAGCACAGGCTTCTGgtgagcgctccgcggcctccgggacccccctggccgcacggggagagctcgggcgcccccctgactgcgcactgtgagagcttcagagaccggagctccctc 840
ctctggggccctggctctcccgggcccgcccccgccgtgtttgtgggtgggtcctccacctgagtgggcgccggggcgtgagcctgggccgccccctgcagcccaggccgatgcccggg 960
atcctgctctttgaggtaaaccaggagtctcccctgggagtggacggccctgcagcgggacctggcctgcctgtcccattccttccacctagagctgaggtacccgccttcctggcaggg 1080
ccagggccagggctggcgttggcccctcgtcttactgctgctgccgttccccatgaagatgggacctccccacattcctggccctaagggtcattttattagtcactgaacgcacgggca 1200
gcgcctggatcctgcgcccgggcagtcctgggcttgaacgtgtgtgtcagccgcgctgccagccatgctgaggctcgggactgagccgccccttgttgtccccagCCCCCCGCTGCCAC 1320
ACAGCCAGGCTGACCAGTACGTCCTCAGCTGGGACCAGCAGCTCAACCTCGCCTATGTGGGCGCCGTCCCTCACCGCGGCATCAAGCAGGTCCGGACCCACTGGCTGCTGGAGCTTGTCA 1440
CCACCAGgtgggcggcgggcagggtctgggcgtcccagagccccttacagaggcacagatgggaggggagggctgggggctgctcggaagaccccttgttcccccacctcccgccgaagc 1560
accctgttggggagagcgtgtccttgctggctgtgctggggtgagggctgtgtgctggagggagcccctgcatggggcacggtgggcttcctgcaggtctccctgcaggctcagggttgg 1680
ctgcgccgcacctggctcctggtcacccgtgagcatccctgtgtgtgtctgctggccaggctgggtagggccactgca 1758
```

B tcctgtgcactcatgttgcctcttggggtgtgggaggggaaatggggcactcctgggcctccaggaggtgcagagaaccagggtgaggtgtccaccaggtcctgcctggctcctgacccc 120
tggcccctgctgctcgcgactggcctgcctcgtgccactgagcctcagagccattccgaacccccaccccaagttttccatctcttgatggtgtagggttgggggtctccatgtacaga 240
tactctagttcataccaggccttcatagggttattttccaaggggaagggcccctcgggaagccgggatcggagtcctgtgtggcaccttgcaggctcccacatgctccgttgtggccac 360
ggttccagcctggagcatggagctgtgtgggcaccctgcttcctgacgctgaccgtccttctgcagGGGTCCACTGGACGGGGCCTGAGCTACAACTTCACCCACCTGGACGGTACCT 480
GGACCTTCTCAGGGAGAACCAGCTCCTCCCAGgtgagctgtgggctctgccctcccagcccgcctgcacccccttgccctgcccaccctctccctcacccagcccctctgagtccttgga 600
tgtccattcagggctggccttggtgccggagcacaggcctggcagagcatgggtgtggtgtgtggtgggcggtggggcagccctcctgtgttccagGGTTTGAGCTGATGGCAGCGCCT 720
CGGGCCACTTCACTGACTTTGAGGACAAGCAGCAGGTGTTTGAGTGGAAGGACTTGGTCTCCAGCCTGGCCAGGAGATACATCGgtgggcgagcgcaggccctggggccctggccggggc 840
gggggtactcctgggcaggttgcacccctatcacgcaggctgctgcctggtcaggagatacattggtgggcaggcgcaggcccttgtgggggatgggggtgacaagggataggttggtg 960
gtcggcgcaggccctggggccccaggctgggggtactcctgggcttggtgggtgggcgaaggccctgggcccctggggtgggggtactcctgggcaggctgcacccctatcacccagg 1080
ccgcacccctatcacccaggccgccgcccaggtcttggacccccttgagccagcgcttcctgatgtggggcgggaggctggcctgcatggagatggggttcatcttgagtcagacgccct 1200
tcatcaccttgcaccctccctccgtgggagtcactgaggcgagattcacctgtgctgggggacagcaaggctcctctgcagGTAGGTACGGACTGGCGCATGTTTCCAAGTGGAACTTC 1320
GAGACGTGGAATGAGCCAGACCACCACGACTTTGACAACGTCTCCATGACCATGCAAGgtgtgcaccgcttcctggggtcctgcccggctgaaagggggcagaggaaggcaggagcagag 1440
gctaagccgctcatccccagggcaggtgtagacgcagtgctcccccggcccagGCTTCCTGAACTACTACGATGCCTGCTCGGAGGGTCTGCGCGCCGCCAGCCCCGCCCTGCGGCTGGG 1560
AGGCCCCGGCGACTCCTTCCACACCCCACCGCGATCCCCGCTGAGCTGGGGCCTCCTGCGCCACTGCCACGACGGTACCAACTTCTTCACTGGGGAGGCGGGCGTGCGGCTGGACTACAT 1680
CTCCCTCCACAGGAAGgtgcgccctgcccctccgtccgccccggtgttctgcgccctcagccgctgtgccccgggccgcgctgaccctggtggtgctgaggcggccccgcccgcagGGTG 1800

```
CGCGCAGCTCCATCTCCATCCTGGAGCAGGAGAAGGTCGTCGCGCAGCAGATCCGGCAGCTCTTCCCCAAGTTCGCGGACACCCCCATTTACAACGACGAGGCGGACCCGCTGGTCGGCT 1920
GGTCCCTGCCACAGCCGTGGAGGCGGACGTGACCTACGCGGCCATGGTGGTGAAGgtgggccggcccaacgccctgcgcgcccccggccaccttcctcccgagacgggacaggcgagc 2040
ggtggccgcgccacccggtcccagctgccctggacacccgcagGTCATCGCGCAGCATCAGAACCTGCTACTGGCCAACACCACCTCCGCCTTCCCCTACGCGCTCCTGAGCAACGACAA 2160
TGCCTTCCTGAGCTACCACCCGCACCCCTTCGCGCAGCGCACGCTCACCGCGCGCTTCCAGGTCAACAACACCCGCCCGCCGCACGTGCAGCTGTTGCGCAAGCCGGTGCTCACGGCCAT 2280
GGGGCTGCTGGCGCTGCTGGgtgagccggggccgctggggtgggccggccagggccctccaggctggggagcggctcctgcgaaggccccgctgcggggagcgcacttcctccagccgcg 2400
cgcttcccggggtcggcctccgcgtggcggggcctggggactccttcaccaaggggagggggagcgagtggtgggaggcccggccctgggtcgggggcggctgggcaacgacccacgc 2520
ggcgacggcccccccccgccccgcagATGAGGAGCAGCTCTGGCCGAAGTGTCGCAGGCCGGGACCGTCCTGGACAGCAACCACACGGTGGCGTCCTGGCCAGCGCCCACCGCCCCCA 2640
GGCCCCGGCCGACGCCTGGCGCGCCCGCGGTGCTGATCTACGCGAGCGACGACACCCGCGCCCACCCCAACCGCAGCGTCGCGGTGACCCTGCGGCTGCGCGGGGTGCCCCCCGGCCCCGGg 2760
taagccggggttccagggaggtctctggccccgctggggctctggagggggcggcccggggagccgaggcctgagtgtcaggccccgcagGCCTGGTCTACGTCACGCGCTACCTGGACA 2880
ACGGGCTCTGCAGCCCCGACGGCGAGTGGCGGCGCCTGGCCCGGCCCCGTCTTCCCCACGCAGAGCAGTTCCGGCGCATGCGCGCGGCTGAGgtaggtgggccgcggaggggcgaggggc 3000
cgggccgggccggggtcccggggggtggggtccggggcgggggctccgaggcggtgtgggtgggaggtggagcggtgggccgggggcgttcgccctgaggtcgggccgagcgtccccag 3120
ctcccctggagaaccctgaggaccggccactgcgcccagGACCCGGTGGCCGCGGCGCCCCGCCCCTTACCCGCCGGCGGCCGCCTGACCCTGCCCCCGCGCTGCGGCTGCCGTCGCTT 3240
TTGCTGGTGCACGTGTGTGCGCGCCCCGAGAAGCCGCCCGGGCAGgcaagtggcagtcccctaacccgcgccgcggcccggactccccttccccgacgccatcacagcccttccctcccc 3360
cagGTCACGCGGCTCCGCGCCCTGCCCCTGACCCAAGGGCAGCTGGTTCTGGTCTGGTCGGATGAACACGTGGGCTCCAAgtgcgtgagtggggccgcccctccctctgcctggtcctag 3480
gcaggtccctgggtcccgaccccttcacccatgcggtcactcgggccacttgccgtggcccatcggctccctccctcgccgccctgcgtccctgcccttcaccccacacactgtgggcca 3600
```

C——————————————————————C cgcgccaggccctgccagtggggtgtgggttctcctaggggacatgagatggacattcgggctccagccctctcctgcctgggcaggaagagtgcccaggggctggggaggtgccgccga 3720
ggggcttgagggaatgaggctgtgggtccacgcggcccgtgccctgcctgctcccacctttgaggactgtcttgacccagccttgttcttggcctgacctccccagGTGCCTGTGGACAT 3840
ACGAGATCCAGTTCTCTCAGGACGGTAAGCCGTACACCCCGGTCAGCAGGAAGCCATCGACCTTCAACCTCTTTGTGTTCAGCCCAGgtgcgcccaccacccgctgccctggactcggcc 3960
accccattcttgggcctcagggcagtactgggtgggggcctcgagaagcctggggtcagggggctttcgggtgggggcaggttccggttggcacacatgtccccttgtctccagACACAG 4080
GTGCTGTCTCTGGCTCCTACCGAGTTCGGACCCTGGACTACTGGGCCCGACCAGGCCCCTTCTCGGACCCTGTGCCGTACCTGGAGGTCCCTGTGCCAAGAGGCCCCCATCCCCGGG-A 4200
ATCCATGAgcctgtgctgagccccagtgggttgcacctccaccggcagtcagcgagctggggctgcactgtgcccatgctgccctcccatcacccccttgcaatatatttttatatttt 4320
attatttt-ttttatatcttggtaccaacgcccccttttaaagcggcttgcacaggtcagtctcgggttgaggctctgtggcttggccctgggcacattccagggcagcctccaagggta 4440
aaccccggtggctgatgaggaccagctggagcgaggcct 4480

SEQUENCE LISTING

```
(1) GENERAL INFORMATION:

   (iii) NUMBER OF SEQUENCES: 7


(2) INFORMATION FOR SEQ ID NO:1:

     (i) SEQUENCE CHARACTERISTICS:
          (A) LENGTH: 47 base pairs
          (B) TYPE: nucleic acid
          (C) STRANDEDNESS: single
          (D) TOPOLOGY: linear

    (ii) MOLECULE TYPE: Oligonucleotide DNA

    (xi) SEQUENCE DESCRIPTION: SEQ ID NO:1:

AACTTCGAGA CCTGGAACGA GCCCGACCAG CACGACTTCG ACAACGT                  47


(2) INFORMATION FOR SEQ ID NO:2:

     (i) SEQUENCE CHARACTERISTICS:
          (A) LENGTH: 20 base pairs
          (B) TYPE: nucleic acid
          (C) STRANDEDNESS: single
          (D) TOPOLOGY: linear

    (ii) MOLECULE TYPE: Oligonucleotide DNA

    (xi) SEQUENCE DESCRIPTION: SEQ ID NO:2:

GCCCGGGCGG CRTCCACYTG                                                20


(2) INFORMATION FOR SEQ ID NO:3:

     (i) SEQUENCE CHARACTERISTICS:
          (A) LENGTH: 38 base pairs
          (B) TYPE: nucleic acid
          (C) STRANDEDNESS: single
          (D) TOPOLOGY: linear

    (ii) MOLECULE TYPE: Oligonucleotide DNA

    (xi) SEQUENCE DESCRIPTION: SEQ ID NO:3:

AACCATCAGC AAGCAGGTCA TTGTTCCAAC GCGTGGCC                            38


(2) INFORMATION FOR SEQ ID NO:4:

     (i) SEQUENCE CHARACTERISTICS:
          (A) LENGTH: 2155 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 89..2047

    (xi) SEQUENCE DESCRIPTION: SEQ ID NO:4:

GTCACATGGG GTGCGCGCCC AGACTCCGAC CCGGAGGCGG AACCGGCAGT GCAGCCCGAA     60

GCCCCGCAGT CCCCGAGCAC GCGTGGCC ATG CGT CCC CTG CGC CCC CGC GCC       112
                               Met Arg Pro Leu Arg Pro Arg Ala
                                 1               5

GCG CTG CTG GCG CTC CTG GCC TCG CTC CTG GCC GCG CCC CCG GTG GCC      160
Ala Leu Leu Ala Leu Leu Ala Ser Leu Leu Ala Ala Pro Pro Val Ala
     10                  15                  20
```

-continued

```
CCG GCC GAG GCC CCG CAC CTG GTG CAG GTG GAC GCG GCC CGC GCG CTG      208
Pro Ala Glu Ala Pro His Leu Val Gln Val Asp Ala Ala Arg Ala Leu
 25                  30                  35                  40

TGG CCC CTG CGG CGC TTC TGG AGG AGC ACA GGC TTC TGC CCC CCG CTG      256
Trp Pro Leu Arg Arg Phe Trp Arg Ser Thr Gly Phe Cys Pro Pro Leu
                 45                  50                  55

CCA CAC AGC CAG GCT GAC CAG TAC GTC CTC AGC TGG GAC CAG CAG CTC      304
Pro His Ser Gln Ala Asp Gln Tyr Val Leu Ser Trp Asp Gln Gln Leu
             60                  65                  70

AAC CTC GCC TAT GTG GGC GCC GTC CCT CAC CGC GGC ATC AAG CAG GTC      352
Asn Leu Ala Tyr Val Gly Ala Val Pro His Arg Gly Ile Lys Gln Val
         75                  80                  85

CGG ACC CAC TGG CTG CTG GAG CTT GTC ACC ACC AGG GGG TCC ACT GGA      400
Arg Thr His Trp Leu Leu Glu Leu Val Thr Thr Arg Gly Ser Thr Gly
     90                  95                 100

CGG GGC CTG AGC TAC AAC TTC ACC CAC CTG GAC GGG TAC TTG GAC CTT      448
Arg Gly Leu Ser Tyr Asn Phe Thr His Leu Asp Gly Tyr Leu Asp Leu
105                 110                 115                 120

CTC AGG GAG AAC CAG CTC CTC CCA GGG TTT GAG CTG ATG GGC AGC GCC      496
Leu Arg Glu Asn Gln Leu Leu Pro Gly Phe Glu Leu Met Gly Ser Ala
                125                 130                 135

TCG GGC CAC TTC ACT GAC TTT GAG GAC AAG CAG CAG GTG TTT GAG TGG      544
Ser Gly His Phe Thr Asp Phe Glu Asp Lys Gln Gln Val Phe Glu Trp
            140                 145                 150

AAG GAC TTG GTC TCC AGC CTG GCC AGG AGA TAC ATC GGT AGG TAC GGA      592
Lys Asp Leu Val Ser Ser Leu Ala Arg Arg Tyr Ile Gly Arg Tyr Gly
        155                 160                 165

CTG GCG CAT GTT TCC AAG TGG AAC TTC GAG ACG TGG AAT GAG CCA GAC      640
Leu Ala His Val Ser Lys Trp Asn Phe Glu Thr Trp Asn Glu Pro Asp
    170                 175                 180

CAC CAC GAC TTT GAC AAC GTC TCC ATG ACC ATG CAA GGC TTC CTG AAC      688
His His Asp Phe Asp Asn Val Ser Met Thr Met Gln Gly Phe Leu Asn
185                 190                 195                 200

TAC TAC GAT GCC TGC TCG GAG GGT CTG CGC GCC GCC AGC CCC GCC CTG      736
Tyr Tyr Asp Ala Cys Ser Glu Gly Leu Arg Ala Ala Ser Pro Ala Leu
                205                 210                 215

CGG CTG GGA GGC CCC GGC GAC TCC TTC CAC ACC CCA CCG CGA TCC CCG      784
Arg Leu Gly Gly Pro Gly Asp Ser Phe His Thr Pro Pro Arg Ser Pro
            220                 225                 230

CTG AGC TGG GGC CTC CTG CGC CAC TGC CAC GAC GGT ACC AAC TTC TTC      832
Leu Ser Trp Gly Leu Leu Arg His Cys His Asp Gly Thr Asn Phe Phe
        235                 240                 245

ACT GGG GAG GCG GGC GTG CGG CTG GAC TAC ATC TCC CTC CAC AGG AAG      880
Thr Gly Glu Ala Gly Val Arg Leu Asp Tyr Ile Ser Leu His Arg Lys
    250                 255                 260

GGT GCG CGC AGC TCC ATC TCC ATC CTG GAG CAG GAG AAG GTC GTC GCG      928
Gly Ala Arg Ser Ser Ile Ser Ile Leu Glu Gln Glu Lys Val Val Ala
265                 270                 275                 280

CAG CAG ATC CGG CAG CTC TTC CCC AAG TTC GCG GAC ACC CCC ATT TAC      976
Gln Gln Ile Arg Gln Leu Phe Pro Lys Phe Ala Asp Thr Pro Ile Tyr
                285                 290                 295

AAC GAC GAG GCG GAC CCG CTG GTG GGC TGG TCC CTG CCA CAG CCG TGG     1024
Asn Asp Glu Ala Asp Pro Leu Val Gly Trp Ser Leu Pro Gln Pro Trp
            300                 305                 310

AGG GCG GAC GTG ACC TAC GCG GCC ATG GTG GTG AAG GTC ATC GCG CAG     1072
Arg Ala Asp Val Thr Tyr Ala Ala Met Val Val Lys Val Ile Ala Gln
        315                 320                 325

CAT CAG AAC CTG CTA CTG GCC AAC ACC ACC TCC GCC TTC CCC TAC GCG     1120
His Gln Asn Leu Leu Leu Ala Asn Thr Thr Ser Ala Phe Pro Tyr Ala
```

-continued

```
    330                 335                 340

CTC CTG AGC AAC GAC AAT GCC TTC CTG AGC TAC CAC CCG CAC CCC TTC     1168
Leu Leu Ser Asn Asp Asn Ala Phe Leu Ser Tyr His Pro His Pro Phe
345                 350                 355                 360

GCG CAG CGC ACG CTC ACC GCG CGC TTC CAG GTC AAC AAC ACC CGC CCG     1216
Ala Gln Arg Thr Leu Thr Ala Arg Phe Gln Val Asn Asn Thr Arg Pro
                365                 370                 375

CCG CAC GTG CAG CTG TTG CGC AAG CCG GTG CTC ACG GCC ATG GGG CTG     1264
Pro His Val Gln Leu Leu Arg Lys Pro Val Leu Thr Ala Met Gly Leu
            380                 385                 390

CTG GCG CTG CTG GAT GAG GAG CAG CTC TGG GCC GAA GTG TCG CAG GCC     1312
Leu Ala Leu Leu Asp Glu Glu Gln Leu Trp Ala Glu Val Ser Gln Ala
        395                 400                 405

GGG ACC GTC CTG GAC AGC AAC CAC ACG GTG GGC GTC CTG GCC AGC GCC     1360
Gly Thr Val Leu Asp Ser Asn His Thr Val Gly Val Leu Ala Ser Ala
    410                 415                 420

CAC CGC CCC CAG GGC CCG GCC GAC GCC TGG CGC GCC GCG GTG CTG ATC     1408
His Arg Pro Gln Gly Pro Ala Asp Ala Trp Arg Ala Ala Val Leu Ile
425                 430                 435                 440

TAC GCG AGC GAC GAC ACC CGC GCC CAC CCC AAC CGC AGC GTC GCG GTG     1456
Tyr Ala Ser Asp Asp Thr Arg Ala His Pro Asn Arg Ser Val Ala Val
                445                 450                 455

ACC CTG CGG CTG CGC GGG GTG CCC CCC GGC CCG GGC CTG GTC TAC GTC     1504
Thr Leu Arg Leu Arg Gly Val Pro Pro Gly Pro Gly Leu Val Tyr Val
            460                 465                 470

ACG CGC TAC CTG GAC AAC GGG CTC TGC AGC CCC GAC GGC GAG TGG CGG     1552
Thr Arg Tyr Leu Asp Asn Gly Leu Cys Ser Pro Asp Gly Glu Trp Arg
        475                 480                 485

CGC CTG GGC CGG CCC GTC TTC CCC ACG GCA GAG CAG TTC CGG CGC ATG     1600
Arg Leu Gly Arg Pro Val Phe Pro Thr Ala Glu Gln Phe Arg Arg Met
    490                 495                 500

CGC GCG GCT GAG GAC CCG GTG GCC GCG GCG CCC CGC CCC TTA CCC GCC     1648
Arg Ala Ala Glu Asp Pro Val Ala Ala Ala Pro Arg Pro Leu Pro Ala
505                 510                 515                 520

GGC GGC CGC CTG ACC CTG CGC CCC GCG CTG CGG CTG CCG TCG CTT TTG     1696
Gly Gly Arg Leu Thr Leu Arg Pro Ala Leu Arg Leu Pro Ser Leu Leu
                525                 530                 535

CTG GTG CAC GTG TGT GCG CGC CCC GAG AAG CCG CCC GGG CAG GTC ACG     1744
Leu Val His Val Cys Ala Arg Pro Glu Lys Pro Pro Gly Gln Val Thr
            540                 545                 550

CGG CTC CGC GCC CTG CCC CTG ACC CAA GGG CAG CTG GTT CTG GTC TGG     1792
Arg Leu Arg Ala Leu Pro Leu Thr Gln Gly Gln Leu Val Leu Val Trp
        555                 560                 565

TCG GAT GAA CAC GTG GGC TCC AAG TGC CTG TGG ACA TAC GAG ATC CAG     1840
Ser Asp Glu His Val Gly Ser Lys Cys Leu Trp Thr Tyr Glu Ile Gln
    570                 575                 580

TTC TCT CAG GAC GGT AAG GCG TAC ACC CCG GTC AGC AGG AAG CCA TCG     1888
Phe Ser Gln Asp Gly Lys Ala Tyr Thr Pro Val Ser Arg Lys Pro Ser
585                 590                 595                 600

ACC TTC AAC CTC TTT GTG TTC AGC CCA GAC ACA GGT GCT GTC TCT GGC     1936
Thr Phe Asn Leu Phe Val Phe Ser Pro Asp Thr Gly Ala Val Ser Gly
                605                 610                 615

TCC TAC CGA GTT CGA GCC CTG GAC TAC TGG GCC CGA CCA GGC CCC TTC     1984
Ser Tyr Arg Val Arg Ala Leu Asp Tyr Trp Ala Arg Pro Gly Pro Phe
            620                 625                 630

TCG GAC CCT GTG CCG TAC CTG GAG GTC CCT GTG CCA AGA GGG CCC CCA     2032
Ser Asp Pro Val Pro Tyr Leu Glu Val Pro Val Pro Arg Gly Pro Pro
        635                 640                 645

TCC CCG GGC AAT CCA TGAGCCTGTG CTGAGCCCCA GTGGGTTGCA CCTCCACCGG     2087
```

-continued

```
Ser Pro Gly Asn Pro
    650

CAGTCAGCGA GCTGGGGCTG CACTGTGCCC ATGCTGCCCT CCCATCACCC CCTTTGCAAT   2147

ATATTTTT                                                            2155
```

(2) INFORMATION FOR SEQ ID NO:5:

(i) SEQUENCE CHARACTERISTICS:
(A) LENGTH: 653 amino acids
(B) TYPE: amino acid
(D) TOPOLOGY: linear (ii) MOLECULE TYPE: protein (xi) SEQUENCE DESCRIPTION: SEQ ID NO:5:

```
Met Arg Pro Leu Arg Pro Arg Ala Ala Leu Leu Ala Leu Leu Ala Ser
  1               5                  10                  15

Leu Leu Ala Ala Pro Pro Val Ala Pro Ala Glu Ala Pro His Leu Val
             20                  25                  30

Gln Val Asp Ala Ala Arg Ala Leu Trp Pro Leu Arg Arg Phe Trp Arg
         35                  40                  45

Ser Thr Gly Phe Cys Pro Pro Leu Pro His Ser Gln Ala Asp Gln Tyr
     50                  55                  60

Val Leu Ser Trp Asp Gln Gln Leu Asn Leu Ala Tyr Val Gly Ala Val
 65                  70                  75                  80

Pro His Arg Gly Ile Lys Gln Val Arg Thr His Trp Leu Leu Glu Leu
                 85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320
```

-continued

```
Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
    370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650
```

(2) INFORMATION FOR SEQ ID NO:6:

(i) SEQUENCE CHARACTERISTICS:
(A) LENGTH: 1758 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

```
TTAAATATGT ATATTCGTAT TGCTTTGGCT TAAACAATAT TTCAGTCCTG CCTTGGTTGA      60

ATCCATGGAT CTGAAGCCAA GTGTAAGGAG GGCCCAGTGT GCTCTTCTGG GGTAATTCTC     120
```

-continued

```
CTTCCTGCTA AAGCGCACGC TTTACTCAGG AGGCTGGGGT GAGAAAATCG CTGAAGCCCC    180

GGAGATGGAG GTTGCAGTGA GCTGAGATCG CGCCACTGCA CCTCAGCCTG GGCGACAAAG    240

CAAGACTCTG TCTCAAAAAC ACACAAAAAC AGAGAAAAAC AAGACAGTAA TGGCTCAACT    300

CACATAGCAC CAACGGGCGA AGCGTTCTTC TGAGCGCTTT CCGAGTCATC GGTCCTCAGA    360

GCAGCCCCTG AGGCCCGCAA GGAAGCGGGG CTCCAAGCCC TGCCGTGCTC CCGGCTCCCC    420

GAGGCTCCCC GAGGCCACCC AACCCCTCCC ACCCGGCCAT CGCCCCCTCA CCAAGGCCCC    480

GCCCCGCGGC GGCGGTCACA TGGGGTGCGC GCCCAGACTC CGACCCGGAG GCGGAACCGG    540

CAGTGCAGCC CGAAGCCCCG CAGTCCCCGA GCACGCGTGG CCATGCGTCC CCTGCGCCCC    600

CGCGCCGCGC TGCTGGCGCT CCTGGCCTCG CTCCTGGCCG CGCCCCCGGT GGCCCCGGCC    660

GAGGCCCCGC ACCTGGTGCA GGTGGACGCG GCCCGCGCGC TGTGGCCCCT GCGGCGCTTC    720

TGGAGGAGCA CAGGCTTCTG GTGAGCGCTC CGCGGCCTCC GGGACCCCCT GGCCGCACGG    780

GGAGAGCTCG GGCGCCCCCT GACTGCGCAC TGTGAGAGCT TCAGAGACCG GAGCTCCCTC    840

CTCTGGGGCC CTGGCTCTCC CGGGCCCGCC CCCCGCCGTG TTTGTGGGTG GGTCCTCCAC    900

CTGAGTGGGC GCCGGGGCGT GAGCCTGGGC CGCCCCCTGC AGCCCAGGCC GATGCCCGGG    960

ATCCTGCTCT TTGAGGTAAA CCAGGAGTCT CCCCTGGGAG TGGACGGCCC TGCAGCGGGA   1020

CCTGGCCTGC CTGTCCCATT CCTTCCACCT AGAGCTGAGG TACCCGCCTT CCTGGCAGGG   1080

CCAGGGCCAG GGCTGGCGTT GGCCCCTCGT CTTACTGCTG CTGCCGTTCC CCATGAAGAT   1140

GGGACCTCCC CACATTCCTG GCCCTAAGGG TCATTTTATT AGTCACTGAA CGCACGGGCA   1200

GCGCCTGGAT CCTGCGCCCG GGCAGTCCTG GGCTTGAACG TGTGTGTCAG CCGCGCTGCC   1260

AGCCATGCTG AGGCTCGGGA CTGAGCCGCC CCTTTGTTGT CCCCAGCCCC CCGCTGCCAC   1320

ACAGCCAGGC TGACCAGTAC GTCCTCAGCT GGGACCAGCA GCTCAACCTC GCCTATGTGG   1380

GCGCCGTCCC TCACCGCGGC ATCAAGCAGG TCCGGACCCA CTGGCTGCTG GAGCTTGTCA   1440

CCACCAGGTG GGCGGCGGGC AGGGTCTGGG CGTCCCAGAG CCCCTTACAG AGGCACAGAT   1500

GGGAGGGGAG GGCTGGGGGC TGCTCGGAAG ACCCCTTGTT CCCCCACCTC CCGCCGAAGC   1560

ACCCTGTTGG GGAGAGCGTG TCCTTGCTGG CTGTGCTGGG GTGAGGGCTG TGTGCTGGAG   1620

GGAGCCCCTG CATGGGGCAC GGTGGGCTTC CTGCAGGTCT CCCTGCAGGC TCAGGGTTGG   1680

CTGCGCCGCA CCTGGCTCCT GGTCACCCGT GAGCATCCCT GTGTGTGTCT GCTGGCCAGG   1740

CTGGGTAGGG CCACTGCA                                                 1758
```

(2) INFORMATION FOR SEQ ID NO:7:

(i) SEQUENCE CHARACTERISTICS:
(A) LENGTH: 4480 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

```
TCCTGTGCAC TCATGTTGCC TCTTGGGGTG TGGGAGGGGA AATGGGGCAC TCCTGGGCCT     60

CCAGGAGGTG CAGAGAACCA GGGTGAGGTG TCCACCAGGT CCTGCCTGGC TCCTGACCCC    120

TGGCCCCTGC TGCTCGCGAC TGGCCTGCCT CGTGCCACTG AGCCTCAGAG CCATTCCGAA    180

CCCCCACCCC AAGTTTTCCA TCTCTTGATG GTGTAGGGTT GGGGGGTCTC CATGTACAGA    240

TACTCTAGTT CATACCAGGC CTTCATAGGG TTATTTTCCA AGGGGAAGGG CCCCTCGGGA    300
```

-continued

```
AGCCGGGATC GGAGTCCTGT GTGGCACCTT GCAGGCTCCC ACATGCTCCG TTGTGGCCAC    360
GGTTCCAGCC TGGAGCATGG AGCTGTGTGG GCACCCTGCT TCCTGACGCT GACCGTCCTT    420
CTGCAGGGGG TCCACTGGAC GGGGCCTGAG CTACAACTTC ACCCACCTGG ACGGGTACCT    480
GGACCTTCTC AGGGAGAACC AGCTCCTCCC AGGTGAGCTG TGGGCTCTGC CCTCCCAGCC    540
CGCCTGCACC CCCTTGCCCT GCCCACCCTC TCCCTCACCC AGCCCCTCTG AGTCCTTGGA    600
TGTCCATTCA GGGCTGGCCT TGGTGCCGGA GCACAGGCCT GGCAGAGCAT GGGTGTGGTG    660
TGTGGTGGGC GGTGGGGCAG CCCTCCTGTG TTCCAGGGTT TGAGCTGATG GGCAGCGCCT    720
CGGGCCACTT CACTGACTTT GAGGACAAGC AGCAGGTGTT TGAGTGGAAG GACTTGGTCT    780
CCAGCCTGGC CAGGAGATAC ATCGGTGGGC GAGCGCAGGC CCTGGGGCCC TGGCCGGGGC    840
GGGGGTACTC CTGGGCAGGT TGCACCCCTA TCACGCAGGC TGCTGCCTGG TCAGGAGATA    900
CATTGGTGGG CAGGCGCAGG CCCTTGTGGG GGGATGGGGG TGACAAGGGA TAGGTTGGTG    960
GTCGGCGCAG GCCCTGGGGC CCCAGGCTGG GGGGTACTCC TGGGCTTGGT GGGTGGGCGA   1020
AGGCCCTGGG CCCCTGGGGT GGGGGGTACT CCTGGGCAGG CTGCACCCCT ATCACCCAGG   1080
CCGCACCCCT ATCACCCAGG CCGCCGCCCA GGTCTTGGAC CCCCTTGAGC CAGCGCTTCC   1140
TGATGTGGGG CGGGAGGCTG GCCTGCATGG AGATGGGGTT CATCTTGAGT CAGACGCCCT   1200
TCATCACCTT GCACCCTCCC TCCGTGGGAG TCACTGAGGC GAGATTCACC TGTGCTGGGG   1260
GGACAGCAAG GCTCCTCTGC AGGTAGGTAC GGACTGGCGC ATGTTTCCAA GTGGAACTTC   1320
GAGACGTGGA ATGAGCCAGA CCACCACGAC TTTGACAACG TCTCCATGAC CATGCAAGGT   1380
GTGCACCGCT TCCTGGGGTC CTGCCCGGCT GAAAGGGGGC AGAGGAAGGC AGGAGCAGAG   1440
GCTAAGCCGC TCATCCCCAG GGCAGGTGTA GACGCAGTGC TCCCCCGGCC CAGGCTTCCT   1500
GAACTACTAC GATGCCTGCT CGGAGGGTCT GCGCGCCGCC AGCCCCGCCC TGCGGCTGGG   1560
AGGCCCCGGC GACTCCTTCC ACACCCCACC GCGATCCCCG CTGAGCTGGG GCCTCCTGCG   1620
CCACTGCCAC GACGGTACCA ACTTCTTCAC TGGGGAGGCG GGCGTGCGGC TGGACTACAT   1680
CTCCCTCCAC AGGAAGGTGC GCCCTGCCCC TCCGTCCGCC CCGGTGTTCT GCGCCCTCAG   1740
CCGCTGTGCC CCGGGCCGCG CTGACCCTGG TGGTGCTGAG GCGGCCCCGC CCGCAGGGTG   1800
CGCGCAGCTC CATCTCCATC CTGGAGCAGG AGAAGGTCGT CGCGCAGCAG ATCCGGCAGC   1860
TCTTCCCCAA GTTCGCGGAC ACCCCCATTT ACAACGACGA GGCGGACCCG CTGGTGGGCT   1920
GGTCCCTGCC ACAGCCGTGG AGGGCGGACG TGACCTACGC GGCCATGGTG GTGAAGGTGG   1980
GCCGGCCCAA CGCCCTGCGC GCCCCCCGGC CACCTTCCTC CCGAGACGGG ACAGGCGAGC   2040
GGTGGCCGCG CCACCCGGTC CCAGCTGCCC TGGACACCCG CAGGTCATCG CGCAGCATCA   2100
GAACCTGCTA CTGGCCAACA CCACCTCCGC CTTCCCCTAC GCGCTCCTGA GCAACGACAA   2160
TGCCTTCCTG AGCTACCACC CGCACCCCTT CGCGCAGCGC ACGCTCACCG CGCGCTTCCA   2220
GGTCAACAAC ACCCGCCCGC CGCACGTGCA GCTGTTGCGC AAGCCGGTGC TCACGGCCAT   2280
GGGGCTGCTG GCGCTGCTGG GTGAGCCGGG GCCGCTGGGG TGGGCCGGCC AGGGCCCTCC   2340
AGGCTGGGGA GCGGCTCCTG CGAAGGCCCC GCTGCGGGGA GCGCACTTCC TCCAGCCGCG   2400
CGCTTCCCGG GGTCGGCCTC CGCGTGGCGG GGCCTGGGGA CTCCTTCACC AAGGGGAGGG   2460
GGAGCGAGTG GTGGGAGGCC CGGCCCTGGG TCGGGGGGCG GCTGGGCAAC GACCCCACGC   2520
GGCGACGGCC CCCCCCCGCC CCGCAGATGA GGAGCAGCTC TGGGCCGAAG TGTCGCAGGC   2580
CGGGACCGTC CTGGACAGCA ACCACACGGT GGGCGTCCTG GCCAGCGCCC ACCGCCCCCA   2640
```

-continued

```
GGGCCCGGCC GACGCCTGGC GCGCCGCGGT GCTGATCTAC GCGAGCGACG ACACCCGCGC   2700
CCACCCCAAC CGCAGCGTCG CGGTGACCCT GCGGCTGCGC GGGGTGCCCC CCGGCCCGGG   2760
TAAGCCGGGG TTCCAGGGAG GTCTCTGGCC CCGCTGGGGC TCTGGAGGGG GCGGCCCGGG   2820
GAGCCGAGGC CTGAGTGTCA GGCCCCGCAG GCCTGGTCTA CGTCACGCGC TACCTGGACA   2880
ACGGGCTCTG CAGCCCCGAC GGCGAGTGGC GGCGCCTGGG CCGGCCCGTC TTCCCCACGG   2940
CAGAGCAGTT CCGGCGCATG CGCGCGGCTG AGGTAGGTGG GCCGCGGAGG GGCGAGGGGC   3000
CGGGCCGGGC CGGGGTCCCG GGGGGGTGGG GTCCGGGGCG GGGGCTCCGA GGCGGTGTGG   3060
GTGGGAGGTG GAGCGGTGGG CCGGGGGCGT TCGCCCTGAG GTCGGGCCGA GCGTCCCCAG   3120
CTCCCCTGGA GAACCCTGAG GACCGGCCAC TGCGCCCAGG ACCCGGTGGC CGCGGCGCCC   3180
CGCCCCTTAC CCGCCGGCGG CCGCCTGACC CTGCGCCCCG CGCTGCGGCT GCCGTCGCTT   3240
TTGCTGGTGC ACGTGTGTGC GCGCCCCGAG AAGCCGCCCG GGCAGGCAAG TGGCAGTCCC   3300
CTAACCCGCG CCGCGGCCCG GACTCCCCTT CCCCGACGCC ATCACAGCCC TTCCCTCCCC   3360
CAGGTCACGC GGCTCCGCGC CCTGCCCCTG ACCCAAGGGC AGCTGGTTCT GGTCTGGTCG   3420
GATGAACACG TGGGCTCCAA GTGCGTGAGT GGGGCCGCCC CTCCCTCTGC CTGGTCCTAG   3480
GCAGGTCCCT GGGTCCCGAC CCCTTCACCC ATGCGGTCAC TCGGGCCACT TGCCGTGGCC   3540
CATCGGCTCC CTCCCTCGCC GCCCTGCGTC CCTGCCCTTC ACCCCACACA CTGTGGGCCA   3600
CGCGCCAGGC CCTGCCAGTG GGGTGTGGGT TCTCCTAGGG GACATGAGAT GGACATTCGG   3660
GCTCCAGCCC TCTCCTGCCT GGGCAGGAAG AGTGCCCAGG GGCTGGGGAG GTGCCGCCGA   3720
GGGGCTTGAG GGAATGAGGC TGTGGGTCCA CGCGGCCGTG CCCTGCCTGC TCCCACCTTT   3780
GAGGACTGTC TTGACCCCAG CCTTGTTCTT GGCCTGACCT CCCCAGGTGC CTGTGGACAT   3840
ACGAGATCCA GTTCTCTCAG GACGGTAAGG CGTACACCCC GGTCAGCAGG AAGCCATCGA   3900
CCTTCAACCT CTTTGTGTTC AGCCCAGGTG CGCCCACCAC CCGCTGCCCT GGACTCGGCC   3960
ACCCCATTCT TGGGCCTCAG GGCAGTACTG GGTGGGGGCC TCGAGAAGCC TGGGGTCAGG   4020
GGGCTTTCGG GTGGGGGCAG GTTCCGGTTG GCACACATGT CCCCTTGTCT CCAGACACAG   4080
GTGCTGTCTC TGGCTCCTAC CGAGTTCGGA CCCTGGACTA CTGGGCCCGA CCAGGCCCCT   4140
TCTCGGACCC TGTGCCGTAC CTGGAGGTCC CTGTGCCAAG AGGGCCCCCA TCCCCGGGCA   4200
ATCCATGAGC CTGTGCTGAG CCCCAGTGGG TTGCACCTCC ACCGGCAGTC AGCGAGCTGG   4260
GGCTGCACTG TGCCCATGCT GCCCTCCCAT CACCCCCTTT GCAATATATT TTTATATTTT   4320
ATTATTTTCT TTTATATCTT GGTACCAACG CCCCCTTTAA AGCGGCTTTG CACAGGTCAG   4380
TCTCGGGTTG AGGCTCTGTG GCTTGGCCCT GGGCACATTC CAGGGCAGCC TCCAAGGGTA   4440
AACCCCGGTG GCTGATGAGG ACCCAGCTGG AGCGAGGCCT                         4480
```

SYNTHETIC α-L-IDURONIDASE AND GENETIC SEQUENCES ENCODING SAME

The present application is a continuation application of Ser. No. 08/494,104 filed on Jun. 23, 1995, now abandoned, which is a continuation of Ser. No. 08/084,254 filed on Jul. 7, 1993, now abandoned, which is a 371 application of PCT/AU92/00611, having an international filing filing date of Nov. 12, 1992.

The present invention relates generally to α-L-iduronidase and to genetic sequences encoding same and to the use of these in the investigation, diagnosis and treatment of subjects suspected of or suffering from α-L-iduronidase deficiency.

The lysomal enzyme α-L-iduronidase (IDUA; glycosaminoglycan α-L-iduronohydrolase, EC 3.2.1.76) hydrolyzes the nonreducing terminal α-L-iduronide glycosidic bonds in the glycosaminoglycans heparan sulfate and dermatan sulfate (1,2). IDUA has served as a model for process and maturation events undergone by lysosomal enzymes (3–8). A deficiency of IDUA in humans results in the Jysosomal storage disorder mucopolysaccharidosis type I (MPS-I; cp-onyms, Hurler, Hurler/Scheic, and Scheic syndromes), which is inherited as an autosomal recessive disease and shows wide variation of clinical presentation. Severely affected patients have mental retardation, somatic tissue complications and a reduced life span, while mildly affected patients may have only mild somatic complications and a normal life span. Multiple different mutant alleles at the IDUA locus are thought to be responsible for the spectrum of clinical phenotypes (1,9), but biochemical characterisation of the residual IDUA activity has enabled discrimination only between the extremes of clinical phenotypes (10–12). In work leading up to the present invention, the isolation of the IDUA gene was undertaken to provide a DNA probe for molecular analysis of mutations in MPS-I patients and for use in enzyme and gene therapy experiments in the canine model (1,3) of MPS-I.

Accordingly, the present invention provides an isolated nucleic acid molecule comprising a sequence of nucleotides which encodes, or are complementary to a sequence which encodes, a mammalian α-L-iduronidase (IDUA) or fragment or derivative thereof or its like molecule.

Preferably, the mammal is a human, livestock animal, companion animal, wild animal or laboratory test animal (e.g. rabbit, rat, mouse or guinea pig). Most preferably, the mammal is a human. Conveniently, the IDUA is isolatable from the liver. However, the present invention extends to all mammalian IDUA enzymes and from any anatomical or cellular source and/or any biological fluid source, such as but not limited to plasma, serum, cell extract or lymph fluid.

Although a preferred embodiment of the present invention contemplates the use of human IDUA or genomic or recombinant genetic sequences encoding same in the investigation, diagnosis and/or treatment of human subjects (i.e. homologous system), one skilled in the art will appreciate that the enzyme or genetic sequences encoding same from a non-human animal may also be useful. Such a heterologous system is encompassed by the present invention.

The "nucleic acid molecule" of the present invention may be RNA or DNA (eg. cDNA), single or double stranded and linear or covalently closed. The nucleic acid molecule may also be genomic DNA corresponding to the entire gene or a substantial portion thereof or to fragments and derivatives thereof. The nucleotide sequence may correspond to the nautrally occurring nucleotide sequence or may contain single or multiple nucleotide substitutions, deletions and/or additions. AU such modifications encode the IDUA-like molecules contemplated by the present invention. The length of the nucleotide sequence may vary from a few bases, such as in nucleic acid probes or primers, to a full length sequence.

The nucleic acid molecule of the present invention may constitute solely the nucleotide sequence encoding IDUA or like molecule or may be part of a larger nucleic acid molecule and extends to the genomic clone of IDUA. The non-IDUA encoding sequences in a larger nucleic acid molecule may include vector, promoter, terminator, enhancer, replication or signal sequences or non-coding regions of the genomic clone.

The present invention is particularly directed to the nucleic acid in cDNA form and particularly when inserted in an expression vector. The expression vector may be replicable in a eukaryotic or prokaryotic cell and may either produce mRNA or the mRNA may be subsequently translated into IDUA or like molecule. Particularly preferred eukaryotic cells include CHO cells but may be in any other suitable mammalian cells or cell lines or non-mammalian cells such as yeast or insect cells.

The present invention is further directed to synthetic IDUA or like molecule. The term "synthetic" includes recombinant forms and molecules produced by the sequential addition of amino acid residues, or groups of amino acid residues, in defined order. In a most preferred embodiment, the invention relates to recombinant IDUA or like molecule encoded by or expressed from the nucleic acid molecules as hereinbefore described.

The synthetic or recombinant MUA may comprise an amino acid sequence corresponding to the naturally occurring amino acid sequence or may contain single or multiple amino acid substitutions, deletions and/or additions. The length of the amino acid sequence may range from a few residues to a full length molecule. Accordingly, this aspect of the present invention contemplates a proteinaceous molecule comprising an amino acid sequence corresponding to the full length mammalian IDUA enzyme or to a like molecule. The like molecule, therefore, comprises parts, derivatives and/or portions of the IDUA enzyme whether functional or not. Preferably, the mammal is human but may be of non-human origin as contemplated above.

Advantageously, the recombinant IDUA is a biologically pure preparation meaning that it has undergone some purification away for other proteins and/or non-proteinacous material. The purity of the preparation may be represented as at least 40% of the enzyme, preferably at least 60%, more preferably at least 75%, even more preferably at least 85% and still more preferably at least 95% relative to non-IDUA material as determined by weight, activity, amino acid homology or similarity, antibody reactivity or other convenient means.

Amino acid insertional derivatives of IDUA of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with the following Table 1:

TABLE 1

Suitable residues for amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Where the enzyme is derivatised by amino acid substitution, the amino acids are generally replaced by other amino acids having like properties such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield synthesis) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently elsewhere described such as Sambrook et 1989 *Molecular Cloning: A Laboratory Manual* Cold Spring Harbor Laboratories, Cold Spring Harbor, N.Y.

The derivatives or like molecules include single or multiple substitutions, deletions and/or additions of any component(s) naturally or artificially associated with the IDUA enzyme such as carbohydrate, lipid and/or other proteinaceous moieties. For example, the present invention extends to glycosylated and non-glycosylated forms of the molecule. All such molecules are encompassed by the expression “mutants”, “derivatives”, “fragments”, “portions” and “like” molecules. These molecules may be active or non-active and may contain specific regions, such as a catalytic region. Particularly, preferred derivative molecules include those with altered glycosylation patterns relative to the naturally occurring molecule. Even more particularly, the recombinant molecule is more highly glycosylated than the naturally occurring molecule. Such highly glycosylated derivatives may have improved take-up properties and enhanced half-lives.

The present invention also extends to synthetic IDUA or like molecules when fused to other proteinaceous molecules. The latter may include another enzyme, reporter molecule, purification site or an amino acid sequence which facilitates transport of the molecule out of a cell, such as a signal sequence.

In a most preferred embodiment, the present invention has an amino acid or corresponding IDUA cDNA nucleotide sequence substantially as setforth in FIG. 2 or genomic nucleotide sequence substantially as set forth in FIGS. 4A and 4B or having at least 40% similarity, preferably at least 60% similarity thereto or more preferably at least 80% or 85–90% similarity thereto.

The present invention further contemplates antibodies to synthetic IDUA or like molecule. The antibodies may be polyclonal or monoclonal, naturally occurring or synthetic (including recombinant, fragment or fusion forms). Such antibodies will be useful in developing immunoassays for IDUA.

A further aspect of the present invention contemplates a method of screening for abberations in the IDUA gene. Such a method may be accomplished in a number of ways including isolating a source of DNA to be tested or mRNA therefrom and hybridising thereto a nucleic acid molecule as hereinbefore described. Generally, the nucleic acid is probe or primer size and polymerase chain reaction is a convenient means by which to analyse the RNA or DNA. Other suitable assays include the ligation chain reaction and the strand displacement amplification methods. The IDUA sequence can also be determined and compared to the naturally occurring sequence. Such methods may be useful in adults and children and may be adapted for a pre-natal test. The DNA to be tested includes a genomic sample carrying the IDUA gene, a cDNA clone and/or amplification product.

In accordance with this aspect of the present invention there is provided a method for screening for abberations in the IDUA gene including the absence of such a gene or a portion or a substantial portion thereof comprising isolating a sample of DNA or mRNA corresponding to a region of said DNA and contacting same with an oligonucleotide probe capable of hybridising to one or more complementary sequences within the IDUA gene and then detecting the hybridisation, the extent of hybridisation or the absence of hybridisation. Alternatively, the probe is a primer and capable of directing amplification of one or more regions of said IDUA gene and the amplification products and/or profile of amplification products is compared to an individual carrying the full gene or to a reference date base. Conveniently, the amplification products are sequenced to determine the presence or absence of the full gene.

The present invention further extends to a method of treating patients suffering from IDUA deficiency, such as in MPS-I, said method comprising administering to said patient an effective amount of IDUA or active like form thereof. Preferably, the IDUA is in recombinant form. Such a method is referred to as “enzyme therapy”. Alternatively, gene therapy can be employed including introducing an active gene (i.e. a nucleic acid molecule as hereinbefore described) or to parts of the gene or other sequences which facilitate expression of a naturally occurring IDUA gene.

Administration of the IDUA for enzyme therapy may be by oral, intravenous, suppository, intraperitoneal, intramuscular, intranasal, intradermal or subcutaneous administration or by infusion or implantation. The IDUA is preferably as hereinbefore described including active mutants or derivatives thereof and glycosylation variants thereof. Administration may also be by way of gene therapy including expression of the gene by inclusion of the gene in viral vectors which are introduced into the animal (e.g. human) host to be treated. Alternatively, the gene may be expressed in a bacterial host which is then introduced and becomes part of the bacterial flora in the animal to be tested.

Still yet another aspect of the present invention is directed to a pharmaceutical composition comprising synthetic (e.g. recombinant) IDUA or like molecule, including active derivatives and fragments thereof, alone or in combination with other active molecules. Such other molecules may act synergistically with the enzyme or facilitates its entry to a target cell. The composition will also contain one or more pharmaceutically acceptable carriers and/or diluents. The composition may alternatively comprise a genetic component useful in gene therapy.

The active ingredients of the pharmaceutical composition comprising the synthetic or recombinant IDUA or mutants or fragments or derivatives thereof are contemplated to exhibit excellent activity in treating patients with a deficiency in the enzyme when administered in an amount which depends on the particular case. The variation depends, for example, on the patient and the IDUA used. For example, from about 0.5 ug to about 20 mg of enzyme per animal body or, depending on the animal and other factors, per kilogram of body weight may be administered. Dosage regima may be adjusted to provide the optimum therapeutic response. For example, several divided doses may be administered daily, weekly, monthly or in other suitable time intervals or the dose may be proportionally reduced as indicated by the exigencies of the situation. Accordingly, alternative dosages in the order of 1.0 $\mu$g to 15 mg, 2.0 $\mu$g to 10 mg or 10 $\mu$g to 5 mg may be administered in a single or as part of multiple doses. The active compound may be administered in a convenient manner such as by the oral, intravenous (where water soluble), intramuscular, subcutaneous, intranasal, intradermal or suppository routes or implanting (eg using slow release molecules). Depending on the route of administration,. the active ingredients which comprise a synthetic (e.g. recombinant) IDUA or fragments, derivatives or mutants thereof may be required to be coated in a material to protect same from the action of enzymes, acids and other natural conditions which may inactivate said ingredients. For example, the low lipophilicity of IDUA will allow it to be destroyed in the gastrointestinal tract by enzymes capable of cleaving peptide bonds and in the stomach by acid hydrolysis. In order to administer the vaccine by other than parenteral administration, the enzyme will be coated by, or administered with, a material to prevent its inactivation. For example, the enzyme may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Conveniently, the adjuvant is Freund's Complete or Incomplete Adjuvant. Enzyme inhibitors include pancreatic trypsin inhibitor, diisopropylfluorophosphate (DEP) and trasylol. Liposomes include water-in-oil-in-water CGF emulsions as well as conventional liposomes.

The active compound may also be administered in dispersions prepared in glycerol, liquid polyethylene glycols, and/or mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the IDUA of the present invention is suitably protected as described above, the composition may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in the vaccine compositions is such that a suitable dosage will be obtained. Preferred compositions or preparations according to the present invention are prepared,so that an oral dosage unit form contains between about 0.5 ug and 20 mg of active compound.

The tablets, troches, pills, capsules and the like may also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavoring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release reparations and formulations.

As used herein "pharmaceutically acceptable carriers and/or diluents" include any and all solvents, dispersion media, aqueous solutions, coatings, antibacterial and antifungal agents, isotonic and absorption delaying agents, and the like. The use of such media and agents for pharmaceutical active substances is well known in the art. Except insofar as any conventional media or agent is incompatible with the active ingredient, use thereof in the pharmaceutical compositions is contemplated. Supplementary active ingredients can also be incorporated into the compositions.

The present invention further relates to the use of IDUA or active fragment, mutant or derivative thereof in the manufacture of a medicament for the treatment of patients suffering from a deficiency in the naturally occurring enzyme (e.g. MPS-1).

The present invention is further described with reference to the following non-limiting figures and examples.

BRIEF DESCRIPTION OF THE DRAWINGS

FIG. 4 (SEQ ID NO:6) shows the sequence of the human genomic IDUA gene. Primers were made every 200 to 400 bp to completely sequence areas of interest in both directions. The coding region of the exons are in uppercase letters; untranslated sequence and introns are in lowercase letters. (A) Exons I and II of the human IDUA gene are shown in the 1.8 kb segment. The Alu repeat sequence and the four best potential OC boxes in the promoter region of IDUA are boxed. Potential transcription start sites are underlined. (B) Exons III to XIV of the human IDUA gene are shown in this 4.5 kb segment. Potential polyadenylation signals are underlined.

EXAMPLE

1. MATERIALS AND METHODS

Figure 1:
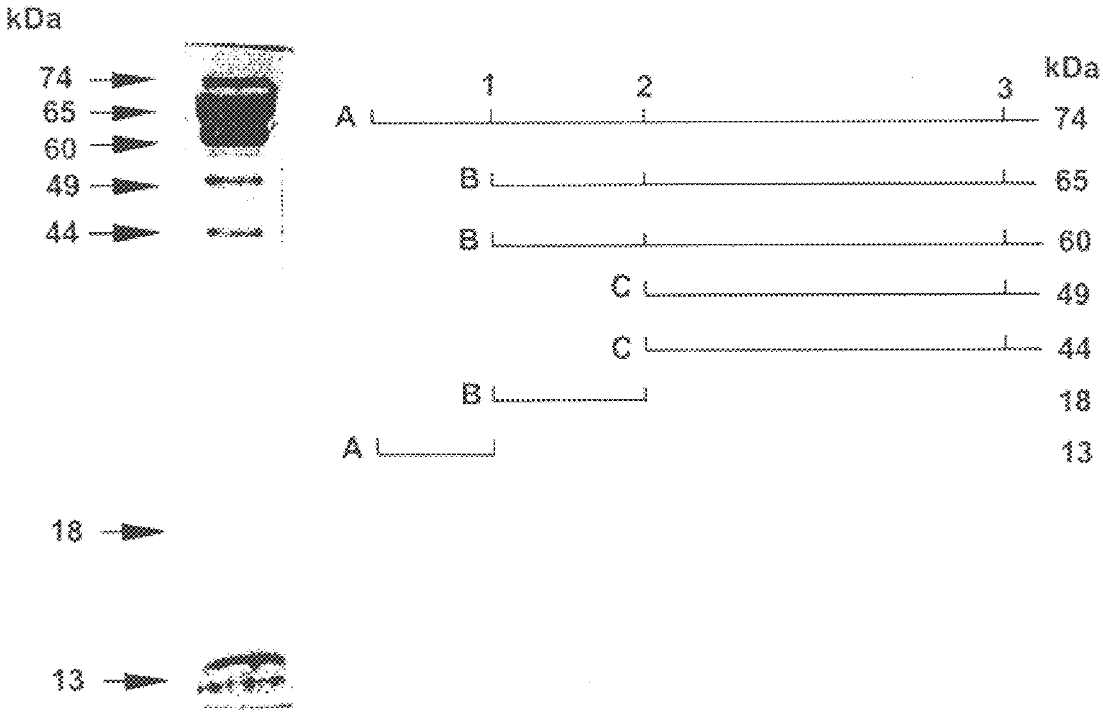
FIG. 1 is a schematic representation showing a model-to connect the seven major polypeptides in immune purified human liver IDUA present after SDS/PAGE as shown on the left, with the polypeptide sizes indicated in kDa (7). The three amino-terminal sequences present are represented by the letters A, B or C next to the polypeptides. The proteolytic sites cleaved to produce the seven polypeptides from the 74-kDa polypeptide are numbered 1, 2 and 3.

Polypeptide Isolation and Sequencing.

All seven major polypeptides of IDUA (7) were directly sequenced from their amino termini as previously described (17). Tryptic peptide sequences from 150 μg of purified human liver IDUA were generated as previously described (18).

Oligonucleotides and Primers.

All oligonucleotides were synthesised on an Applied Biosystems 391 DNA synthesiser. ID47, 5'-AACTTCGAGACCTGGAACGAGCCCGACCAGCACGACTTCGA (SEQ ID NO:1) designed from residue 2 to residue 17 of peptide 8 (see FIG. 2), was used for initial library screening. ID13, 5'-GCCCGGGCGGCA/GTCCACC/TTG-3' (SEQ ID NO:2) (a mixture of four sequences; nucleotides separated by/are options at the same position), designed from residue 13 to residue 7 of the 74/13-kDa amino-terminal amino acid sequence (see FIG. 2), was used to screen Southern blots of the cosmid clone A157.1 (15). IDUA-specific primers used for PCR from cDNA were IDNT, ID39, ID56, ID57, ID58, ID60 and ID61 (see FIG. 2).

Library Screening.

All libraries screened were of human origin and were purchased from Clontech. They were a leukocyte genomic DNA in EMGL3 (catalogue number HL1006) and the following cDNA libraries: colon (random primed, HL1034a), unbilical endothelial (HL1024b), umbilical endothelial. 5' stretch (HL1070b), and T-cell 5' stretch (HL1068b). All libraries were plated at a density of between 40,000 and 55,000 plaques per 140 mm plate. The host cells used for each library were NM538 for the EMBL3 genomic library, C600 for the λgt11 cDNA libraries. Probes were either labelled at the 5' end (19) or labelled by primer extension of random oligonucleotide primers (20) and the Colonyi-Plaquescreen filters (DuPont/NEN) were prehybridised, hybridised, and washed according to the manufacturer's instructions.

Sequencing.

Specific oligonucleotides were made every 200–400 base pairs (bp) to fully sequence fragments in both directions (21). Compressed areas of G+C-rich sequence were resolved by using 7-deazaguanosine (22). Direct PCR sequencing was by the linear PCR method (23).

RNA Isolation and Northern Blot Analysis.

Total RNA was isolated from normal human placental, liver and kidney tissue or cultured normal human fibroblasts as previously described (24). Poly (A)+ RNA was obtained (25) from placental RNA and Northern blotting was carried out on 40 μg of total RNA and 10 and 40 μg of poly (a)+ RNA as described (17).

cDNA Synthesis.

Total RNA (3 μg) from normal fibroblasts was added to a reaction mix containing 1× Moloney murine leukaemia virus (Mo-MLV) reverse transcriptase buffer (BRL), 40 units of RNAsin (Promega), 500 ng of random octamers, 0.5 mM deoxynucleotides (Boehringer Mannheim), and 200 units of Mo-MLV reverse transcriptase (BRL) to a final reaction volume of 50 μ. Incubation at 37° C. for 1 m was followed by hydrolysis of the RNA by the addition of 5 μl of 3 M NaOH and further incubation at 37° for 30 min. The NaOH was neutralised by the addition of 1.25 μl of 10.3 M HCl, and the cDNA was precipitated and resuspended in 50 μl of water. Each PCR used 5 μl of cDNA.

PCR.

PCR reagents were as described by Saiki et al. (26) except that the final concentrations of deoxynucleotides were 400 μM and 10% v/v dimethyl sulfoxide was present in the reaction mix, Forty cycles of denaturation at 94° C. for 45 s, annealing at 58° C. for 43 s, and elongation at 72° C. for 2 min were carried out. PCR products were analysed on 4% w/v Nusieve GTG agarose (FMC) gels.

Construction of Full-Length IDUA cDNA.

cDNA from a mixture of normal human fibroblast cell lines was used for PCR as described, using the primers ID60 and ID6L. ID60 spans the initiating ATG codon and has a HindIII restriction site with a 4 bp GC clamp on the 5' end. ID61 is ≈100 bp 3' of a unique KpnI restriction iste (bases 818–823, see FIG. 2). Utilizing the HindIII and the KpnI sites, the PCR product was directionally cloned in a pTZ19 vector that contained the rest of the IDUA coding sequence from the KpnI site to the EcoRI cloning site of the clone λE8A. In all, 48 clones were analysed and only one was found to be correct (full length). This insert was excised with HindIII and EcoRI and was directionally cloned in the expression vector pRSVN.07 (which drives expression of the insert from the Rous sarcoma virus long terminal repeat) to give pPSVNID7I. This full length IDUA cDNA insert was also subcloned in M13 and sequenced between the HindIII and KpnI restriction sites, using IDUA-specific oligonucleotide primers to determine if any errors were present in the sequence.

Expression of IDUA.

CHO (Chinese hamster ovary) cells (strain DKI) were grown in Ham's F12 medium (GIBCO), 10% v/v fetal calf serum (GOBCO), penicillin at 100 μg/ml streptomycin sulfate at 100 μg/ml, and kanamycin sulfate at 120 μg/ml at 37° C. in a 5% v/v $CO_2$ atmosphere. CHO cells ($1.2 \times 10^7$) were electroporated at 0° C. by using a BRL Cell-Porator at a pulse of 330 μF and 275 V in the presence 15 μg of pRSVNID21. Cells were grown in nonselective medium for 48 hr and then 1:20 and 1:100 dilutions of the electroporated cells were selected in G418 sulfate (Geneticin; GIBCO) at 750 μg/ml. A bulk culture of resistant cells was extracted (14) and assayed for IDUA activity with the fluorogenic substrate 4-methylumbelliferyl α-L-iduronide (Calbiochem) (6). The Bio-Rad protein assay was used to quantitate the amount of protein in each sample according to the manufacturer's instructions. The monoclonal antibody Id1A was used for immunocapture (14) and immunoquantification in conjunction with a polyclonal antibody (12) to assay the specific activity of the expressed IDUA (7).

2. RESULTS

All seven polypeptides of IDUA were subjected to direct arnino-terminal sequencing, and three different amino-terminal sequences were found to be present. The 65-, 60-, and 18-kDa species have a common amino-terminal amino acid sequence, the 49- and 44-kDa another, and the 74- and 13-kDa species another. Assuming that all seven species represent part of a single IDUA polypeptide, a model (FIG. 1), is proposed showing three sites of proteolytic processing of the 74-kDa polypeptide to produce the seven major species of IDUA.

After tryptic digestion and separation by HPLC (18) of immunopurified IDUA, nine major peptides were sequenced. One tryptic peptide was the same as the 65/60/18-kDa amino-terminal sequence, and one of the two tryptic peptide species present in part 3 were contained within the 49/44-kDa amino-terminal sequence. Incorporating choices based on human codon usage and assuming that the undetermined amino acid at position 16 of peptide 8 was a glycosylated asparagine residue (see FIG. 2) the sequence was used to design a 74-mer oligonucleotide (ID47) for library screening.

Using ID47 as a probe, 500,000 clones were screened of the EMBL3 human genomic library and obtained 8 clones. A genomic clone, ID-475, was purified and an ID47-positive 1.6 kilobase (kb) Pst1 fragment was subcloned in pUC19 to produce pID89 (14). This 1.6-kb insert was then used to screen a number of cDNA libraries, this screening yielded only 1 clone, which contained an insert of 729 bp (λRPC1, bases 541–1269;see FIG. 2) from the λgt10 random-promed human colon cDNA library. The sequence of this clone was colinear with six peptide sequences, including the 49/44-kDa amino-terminal sequence, but the clone ended within peptide 9.

The ARPCI insert was then used to screen a λgt11 human endothelial cDNA library. Twenty clones were isolated, and the insert of the longest clone, λE8A, was fully sequenced. The 11765-bp insert contained an open reading frame starting just before the position of the 65/60/18-kDa amino terminus (base 391 in FIG. 2) to a stop codon (base 2048). Six further tryptic peptides were matched to the translated DNA sequence but, significantly, the sequence of the 74/13-kDa amino terminus, a secondary tryptic peptide (peptide Z'), a signal peptide, and an initiating methronine were not present in this -clone. Of the other clones, 7 ended at the same base at the 5' end, while all the others were shorter. A 5' probe derived from λE8A was used to screen another seven cDNA libraries. No clones were obtained from the screening of five of these cDNA libraries. Screening of two 5' "stretch" cDNA libraries (umbilical endothelial and T cell) resulted in a further 38 clones. PCR analysis of these clones showed that all ended at the same 5' base as λE8A. Major secondary structures present in the IDUA mRNA may be responsible for the premature termination of these clones at their 5' ends.

Using the polypeptide model for IDUA (FIG. 1) it was hypothesised that the 74/13-kDa amino-terminal peptide sequence lay at the 5' end of the IDUA mRNA. A mixed oligonucleotide, ID13, made to the 74/13-kDa amino-terminal sequence was used to probe Southern blots of the cosmid A157.1, which spans the area of the IDUA gene (15). A 2.8 kb BamHI fragment was isolated and partially sequenced. The sequence contained an initiating methionine, a signal peptide, 74/13 kDa amino terminus, and the start of the last unmatched tryptic peptide (peptide 2' in FIG. 2). A number of oligonucleotides were made to this exon and PCR used to amplify normal fibroblast cDNA. A major PCR product was obtained between ID58 and ID61, and the oligonucleotides ID56 and ID57, was directly sequenced (23). The collated DNA sequence (FIG. 2) encodes a protein containing all amino-terminal and tryptic peptide sequences obtained from purified IDUA and is consistent with the model for IDUA (FIG. 1).

PCR of normal fibroblast cDNA at the 5' end of the IDUA mRNA, using the oligonucleotides ID58 and ID61, produced a major product representing the sequence described (FIG. 2) and several minor products that also hybridised to an internal oligonucleotide, ID56. This indicates that the minor products were representative of alternative mRNA species from the IDUA gene, as has been reported for a number of other genes, including lysosomal hydrolases (27–29).

Figure 3:
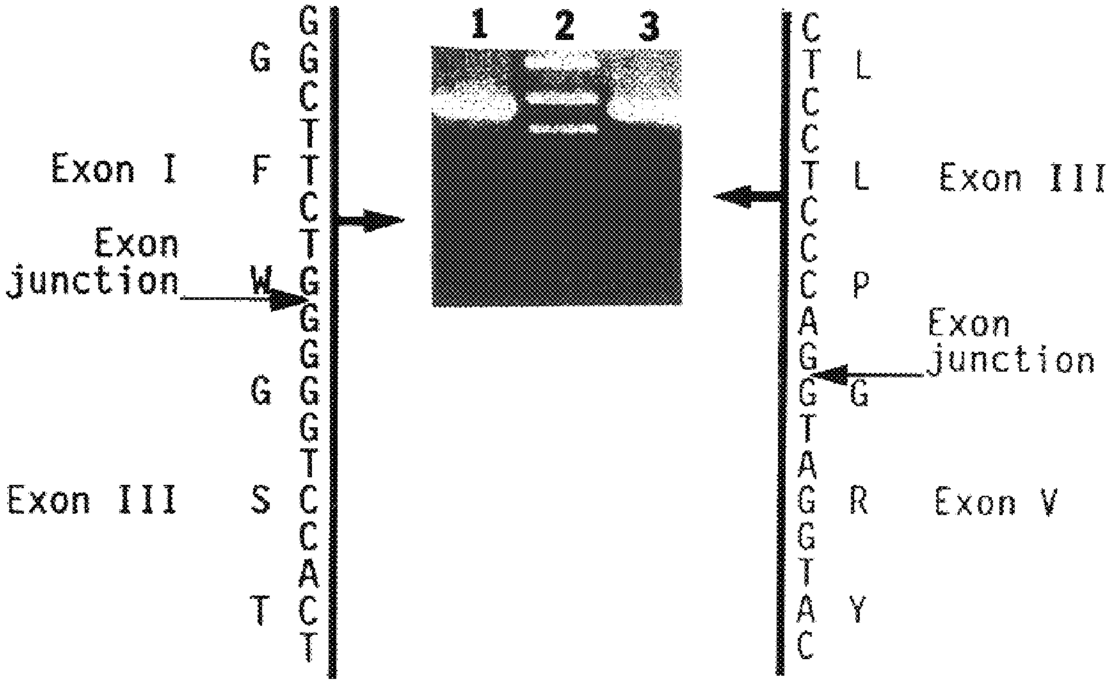
FIG. 3 is a representation of reverse-transcribed normal fibroblast RNA showing the alternative splicing of exons II and IV. Lane 1, PCR between 1D56 and 1D57, howing a major 225-bp product and a minor 84-bp product: lane 2, pUC19 Hpa II markers: lane 3, PCR between IDNT and ID39, showing a major 222-bp product and a minor 114-bp product. Partial sequences of the two minor products and their encoded amino acid are at the left and right of the figures. The position of the missing exon is indicated by the arrow labelled "Exon junction".

PCR of normal fibroblast cDNA using the oligonucleotide pairs ID56 to ID57 and IDNT to ID39 produced two products per reaction. The smaller products were isolated and directly sequenced; they showed alternative splicing of exons II and IV of IDUA (FIG. 3). The polypeptides from these alternatively spliced IDUA mRNA species would maintain the translation frame for the IDUA protein (see FIG. 3) leaving the primary sequence of the translated peptide identical to that of the deduced IDUA peptide except for the omission of 47 and 36 amino acids, respectively. Thus, the alternatively spliced mRNA species individually missing exons II and IV would produce peptide products of 606 and 617 amino acids, respectively.

Using the insert of λESA as a probe against total placental RNA and poly(A)+ RNA, a single 2.3 kb band only was detected when 40 μg of poly(A)+ RNA was loaded in a single track. The strength of the signal also indicated that the mRNA for IDUA has a considerably lower abundance than the iduronate-2-sulfatase mRNA in placental RNA (16). Multiple PCR products of the same relative intensity were observed when reverse-transcribed liver, kidney, or placental RNA was used as template, indicating that this splicing does not appear to be tissue specific and that these products may be minor mRNA species not detectable by Northern blot analysis. The alternative splicing of exon II introduces a tryptophan residue into the amino acid sequence at the splice junction, and the alternative splicing of exons II and IV both interrupt reported peptide sequences (peptide 2' and the 65/60/18 kDa amino terminus of IDUA, respectively, see FIG. 2). Thus, it was thought that the major PCR product was most likely to represent the full-length mRNA encoding IDUA. Expression of this putative full-length mRNA would establish that the nucleotide sequence presented here in FIG. 2 encodes enzymically active IDUA.

PCRs were performed with reverse-transcribed fibroblast RNA as template and the primers ID60 and ID61. The 840 bp PCR product was subcloned in the pTZ19 vector to produce a "full-length" IDUA cDNA clone. Sequence analysis of this full-length insert found four nucleotides that were different from the previously determined sequence. The differences, numbered as in FIG. 2, were A to C (base 276), G to A (base 402), T to C (base 440), and T to C (base 631). The first two differences alter the amino acid residues coded for by the cDNA from Gln to Pro (amino acid 63) and Arg to Gln (amino acid 105), respectively. The T to C (base 440) is a silent change that alters a Leu (amino acid 118) codon from TTG to CTG and introduces a second KpnI site into the cDNA. Thus, the cloned PCR product presumably resulted from partial digestion with KpnI or the ligation of three fragments. The last change T to C (base 631) is a silent change in the third base of an Asn (amino acid 181) codon. All of these differences may be polymorphic, but as two change amino acids, they may be transcription errors introduced by Taq DNA polymerase during PCR in the presence of high concentrations of dNTPs (400 μM) for 40 cycles (30). However, these conditions were essential to produce enough PCR product to conduct the experiment.

This full-length cDNA construct was subcloned in the expression vector pRSVN.07 to produce the construct pRSVNID2L CHO cells were electroporated in the in the presence of pRSVNID21,and G418-resistant colonies were selected and grown as a mass culture. Cellular extracts from control CHO cells, mixed normal human skin fibroblasts, and pRSVNID21 transfected cells were assayed for total IDUA activity by using the IDUA-specific fluorogenic substrate. CHO cell extract contained a low level of IDUA activity. Cellular extract from CHO cells transfected with pRSVNID21 gave a total activity 160-fold greater than the control normal human fibroblast activity (Table 2). To compare the specific activities of the recombinant and fibroblast IDUA serial dilutions of the cellular extracts were assayed in parallel, using human IDUA-specific IDIA monoclonal antibody based immunocapture (14) and ELISA assays (12). The CHO cell extract gave sero background in both assays. The ELISA result was normalized to the normal fibroblast extract and showed a 12.7 fold higher expression of human IDUA in the pRSVNID21 transfected CHO cells. The immunocapture assay showed that this results in an almost proportional increase in IDUA activity in the transfected CHO cells, demonstrating that the normal and recombinant enzymes have similar specific activities (Table 2). These results prove that the IDUA sequence used in this experiment codes for a protein that has a specific activity similar to the IDUA activity present in normal cultured human skin fibroblasts.

TABLE 2

Expression of IDUA

| | IDUA activity[1] | | Relative IDUA | Relative IDUA |
|---|---|---|---|---|
| Cell Type | Total | Captured[4] | protein[2] | specific activity[3] |
| CHO | 1 | ND | ND | — |
| CHO with pRSVNID21 | 160 | 152 | 12.7 | 12.0 |
| Normal human fibroblasts | 16 | 12.6 | 1 | 12.6 |

ND none detected
[1]Activity is in pmol × $10^{-2}$ per min per mg of cell protein
[2]The amount of human IDUA protein captured in the ELISA assay per mg of cell protein normalised against human fibroblasts.
[3]Expressed as IDUA activity relative to IDUA protein.
[4]IDUA activity captured in the immunocapture assay.

A further expression construct was made such that the normal 5' non-coding sequence of the IDUA mRNA, was found in the full length cDNA clone described, was replaced with 30 bp of the 5' non-coding sequence of the rat preproinsulin mRNA (5'-AACCATCAGCAAGCAGGTCATTGTTCCAACGCGTGGCC-3'). At the same time, the four nucleotide differences noted in the PCR-produced 840 bp portion of the original cDNA used for expression (A→C, bp 276;G→A, bp 402; T→C bp 440; T→C bp 631) were corrected. This ensures efficient mRNA translation (34) and has been shown to lead to high-level expression of other lysosomal enzymes in CHO cell expression systems (32,33). This modification also led to greatly enhanced expression of IDUA in CHO-K1 cells. The original expression plasmid was also modified such that the RSV-LTR promoter element was replaced with the human elongation factor 1 α gene promoter from pEFBOS (35). This promoter is 5 times more efficient in CHO-K1 cells than the RSV-LTR.

The total coding sequence, therefore, for IDUA has an open reading frame of 1959 bp encoding a peptide of 653 amino acids. A signal peptide of 26 amino acids with a consensus cleavage site (31) was present immediately adjacent to the mature amino terminus of the protein (74/13 kDa amino terminus). Thus, the mature human IDUA protein of 627 amino acids has a molecular mass of 70,029 Da, which is consistent with the previous estimates of IDUA size after allowing for post-translational modifications (5–8). All major peptide species sequences are present in the translation of the open reading frame, totalling 234 amino acids (42%) of the 627 amino acids of the mature IDUA. This includes several peptides that were present as minor sequences in peptide peaks (secondary peptides, e.g. peptide 7'). The presence of all three amino-terminal sequences from purified human liver IDUA in the peptide sequence presented in FIG. 2 supports the hypothesised model of proteolytic processing of the 74 kDa IDUA polypeptide (FIG. 1). Of six potential stes in the 65/60/18 kDa amino-terminal sequence and peptide 8 was not detected in sequencing and may, therefore, be glycosylated. The potential glycosylation site at the very end of peptide 9 was also not defected, but this may be due to a weak signal towards the end of the sequence rather than a glycosylated residue. No significant homology was found between the human IDUA amino acid sequence and proteins in the GenBank, National Biomedical Research Foundation, or Swiss-Prot data bases (all releases of May, 1991).

Having determined the cDNA sequence, the genomic sequence was then sought. The IDUA genomic sequence is valuable for defining mutations in MPS-1 patients, for defining diagnostically useful polymorphisms for MPS-1 and Huntington's disease and for refining the genetic and physical map of the IDUA gene. The genomic sequence is shown in FIGS. 4A and B as two segments.

The gene for IDUA is split into 14 exons spanning approximately 19 kb. The first 2 exons are separated by a 566 bp intron and the last 12 exons are separated by a 566 bp intron and the last 12 exons are clustered in a 4.2 kb region. Two variant polyadenylation signals consistent with a 2.3 kb mRNA transcript are underlined in FIG. 4B. From the position of the proposed polyadenylation signals, the mRNA produced would be 2203 and 2285 bp with an additional 20–30 prior to the poly(A) tail.

Accordingly, the potential promoter for IDUA is bounded by an Alu repeat sequence and has only GC box type concensus sequences (FIG. 4A).

The full length cDNA and genomic sequence described herein for human IDUA makes it possible to characterise MPS-I mutations and to determine how much of the clinical variability reflects different mutations and how much reflects other genetic or environmental influeneces. Furthermore, large-scale expression of IDUA will provide enzyme for evaluation of eazyrne therapy, for example in the dog model for MPS-I and the cDNA in the appropriate vectors may be used for experimental gene therapy in the same model.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Neufeld, E F & Muenzer, J, (1989) *The Metabolic Basis of Inherimed Disease*, pp 1565–1587.
2. Hopwood, J J, (1989) *Hepain: Chemical and Biological Propenies, Clinical Applications*, pp 190–229.
3. Shapiro, L J, Hall, C W, Leder I J, & Neufeld, E F, (1976) *Arch. Biochem. Biophys*. 172: 156–161.
4. Rome, I H, Garvin, A, Neufeld, E F, (1978) *Arch. Biochem. Biophys*. 189: 344–353.
5. Myerowitz, R, & Neufeld E F, (1981) *J. Biol. Chem*. 256: 3044–3048.
6. Clements, P R, Brooks, D A, Saccone, GTP, & Hopwood, J J, (1985) *Eur, J. Biochem*. 152: 21–28.
7. Clements, P R, Brooks, D A, McCourt, PAG, & Hopwood, J J, (1989) *Biochem. J*. 259: 199–208.
8. Taylor, J A, Gibson, G J, Brooks, D A & Hopwood, J J, (1991) *Biochem. J*. 274: 263–268.
9. Hopwood, J J, & Morris, C P, (1990) *Mol. Biol. Med*. 7: 381–404.
10. Hopwood, J J, & Muller, V, (1979) *Clin. Sci*. 57.265–272.
11. Muller, V, & Hopwood, J J, (1984) *Clin. Genet*. 26: 414–421.
12. Ashton, L W, Brooks, D A, McCourt, PAG, Clements, P R, & Hopwood, J J, (1991) *Am. J. Humn. Genet*. in press
13. Spellacy, E, Shull, R M, Constantopoulos, G, & Neufled, E F (1983) *Proc. Nail. Acad. Sci. USA* 80: 6091–6095.
14. Scott, H S, Ashton, L J, Eyre, H I, Baker, E, Brooks, D A, Callen, D F, Sutherland, G R, Morris, C P & Hopwood, J J, (1990) *Am. J. Hum. Genet*. 47: 802–807.
15. MacDonald, M E, Scott, H S, Whaley, W L, Phol, T, Wasmuth, J J, Lehrach, H, Morris, C P, Frischuaf, A M, Hopwood, J J, & Gusella, J F (1991) *Somaiic Cetl Mol. Genet*. 17: 421–425.
16. Stoltzfus, L Y, Uhrhammer, N, Sosa-Pineda, B, Teplow, D B, & Neufeld, E F, (1990) *Am. J. Hum. Genet*. 47: A147 (abstract 655).
17. Wilson, P J, Morris, C P, Anson, D S,.Occhiodoro, T, Bielicki, J, Clements, P R & Hopwood, J J, (1990) *Proc. Nail. Acad. Sci. USA* 87: 8531–8535.
18. Robertson, D A, Freeman, C, Nelson, P V, Morris, C P, & Hopwood, J J, (1988) *Biochem. Biophys. Res. Cormun*. 157: 218–224.
19. Chaconas, G, & van de Sande, J H, (1980) *Methods Enzyimol*. 65: 75–88.
20. Feinberg, A P, & Vogelstein, B, (1983) *Anal. Biochem*. 132: 6–13.
21. Sanger, F, Nicklen, S, & Coulson, A R, (1977) *Proc. Natl. Acad. Sci. USA* 74: 5463–5467.
22. Mizusawa, S, Nishimura, S, & Seela, F, (1986) *Nucleic Acids Res*. 14: 1319–1324.
23. Murray, V, (1989) *Nucleic Acids Res*. 17: 8889.
24. Chomezynski, P, & Sacchi, N, (1987) *Anal. Biochem*. 162: 156–159.
25. Kingston, R E, (1987) *Current Protocols in Molecidar Biology* pp 4.5.1–4.5.3.
26. Saiki, R K, Gelfand, D H, Stoffel, S, Scharf, S J, Higuchi, R, Horn, G T, Mullis, K B, & Erlich, H A, (1988) *Science* 239: 487–491.
27. Oshima, A, Kyle, J W, Miller, R D, Hoffman, J W, Powell, P, Grubb, J H, Sly, W S, Tropak, M, Guise, S, & Gravel, R A (1987) *Proc. Natl. Acad. Sci. USA* 84: 685–689.
28. Morreau, H, Galjart, N J, Gillemans, N, Willemsen, R, van der Horts, GTJ, & d' Azzo, A, (1989) *J. Biol. Chem*. 264: 20655–20663.
29. Quintern, L E, Schuchman, E H, Levran, O, Suchi, M, Ferlinz, K, Reinke, H, Sandhoff, K, & Desnick, R J, (1989) *EMBO J*. 8: 2469–2473.
30. Eckert, K A, & Kunkel, T A (1990) Nucleic Acids Res. 18: 3739–3744.
31. von Heijne, G, (1986) *Nucleic Acids Res*. 14: 4683–4690.
32. Anson, D S, et al (1992) *Biochem. J*. 284: 789–794.
33. Bielicki, J, et al (1992) *Biochem. J*. (in press).
34. Cullen, B J, (1988) *DNA* 7. 645–650.
35. Mizishima, S, & Nagata, S, (1990) *BAR* 18: 5322.

What is claimed is:

1. A purified α-L-iduronidase (IDUA) wherein the IDUA is secreted and purified from mammalian cells in culture transfected with a DNA sequence encoding human IDUA.

2. The purified IDUA according to claim 1 wherein the mammalian cells are Chinese Hamster Ovary (CHO) cells.

3. The purified IDUA according to claim 1 fused to another proteinaceous molecule.

4. The purified IDUA according to claim 3 wherein said other proteinaceous molecule is at least one of an enzyme, reporter molecule, purification moiety or signal sequence.

5. The purified IDUA according to claim 1 having an amino acid sequence substantially as set forth in FIG. 2 (SEQ ID NO:5).

6. A pharmaceutical composition comprising purified α-L-iduronidase (IDUA) and one or more pharmaceutically acceptable carriers or diluents wherein said IDUA is secreted and purified from mammalian cells in culture transfected with a DNA sequence encoding human IDUA.

7. The pharmaceutical composition according to claim 6 wherein the mammalian cells are CHO cells.

8. The purified IDUA of any of claims 1, 2, 3 or 4 wherein the purified IDUA comprises an enzymatically active fragment thereof.

9. The pharmaceutical composition of claim 6 or 7 wherein said purified IDUA comprises an enzymatically active fragment thereof.

10. The purified IDUA of any of claims 1, 2, 3 or 4 having a purity of at least 95% relative to non-IDUA material as determined by weight, activity, amino acid homology or similarity, antibody reactivity or other convenient means.

11. The pharmaceutical composition of claim 6 or 7 wherein said purified IDUA has a purity of at least 95% relative to non-IDUA material as determined by weight, activity, amino acid homology or similarity, antibody reactivity or other convenient means.

* * * * *

UNITED STATES PATENT AND TRADEMARK OFFICE

CERTIFICATE OF CORRECTION

PATENT NO. : 6,149,909

DATED : November 21, 1999

INVENTOR(S) : Hamish S. Scott, et al

It is certified that error appears in the above-identified patent and that said Letters Patent is hereby corrected as shown below:

Column, 1, line 10, please insert the heading:

-- FIELD OF THE INVENTION -- .

Column 1, line 15, line please insert the heading:

-- BACKGROUND OF THE INVENTION -- .

Column 1, line 39, please insert the heading:

-- SUMMARY OF THE INVENTION -- .

Column 2, line 32, please insert the heading

-- DETAILED DESCRIPTION OF THE INVENTION -- .

UNITED STATES PATENT AND TRADEMARK OFFICE

CERTIFICATE OF CORRECTION

PATENT NO. : 6,149,909

DATED : November 21, 1999

INVENTOR(S) : Hamish S. Scott, et al

Figure 2A:
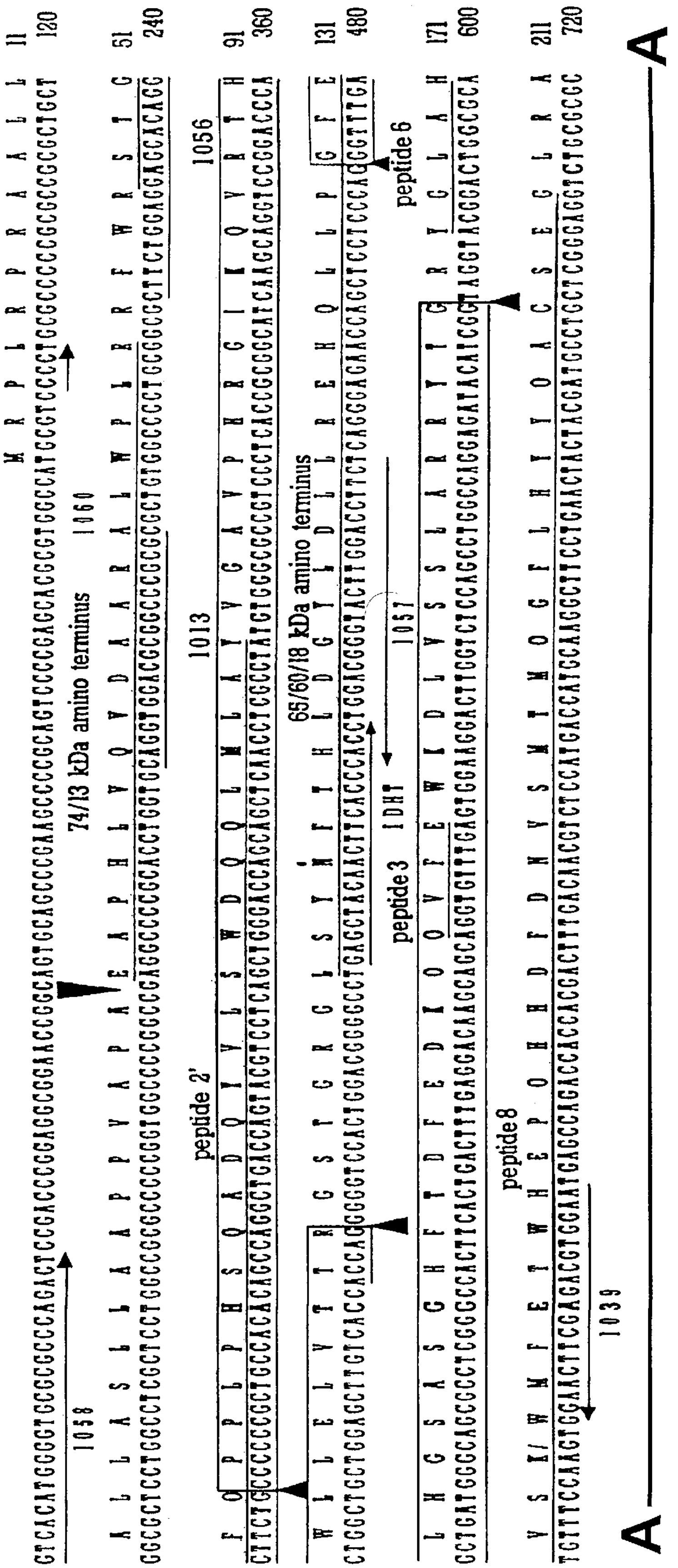
FIG. 2 (SEQ ID NO:4) is a representation of a compiled nucleotide sequence for IDUA cDNA and the deduced amino acid sequence of the protein. The amino acid sequence is shown in single letter code above the cDNA sequence. Nucleotide and amino acid numbers are in the right margin. The probable site of signal peptide peptidase cleavage is shown by a large arrow, and small arrows indicate exon junctions. Exons II and IV, which are alternatively spliced in some RNA transcripts, are boxed. Amino acids colinear with either amino-terminal peptide data or tryptic peptides are underlined and named above the sequence. Potential N-glycosylation sites are asterisked. Oligonucleotides used in this study are underlined below the nucleotide sequence with the arrows indicating either sense (→) or antisense (←). The cDNA clone λRPCI extended from base 541 to base 1269 and λE8A extended from base 391 to the 3' end of the sequence shown.
Figure 2B:
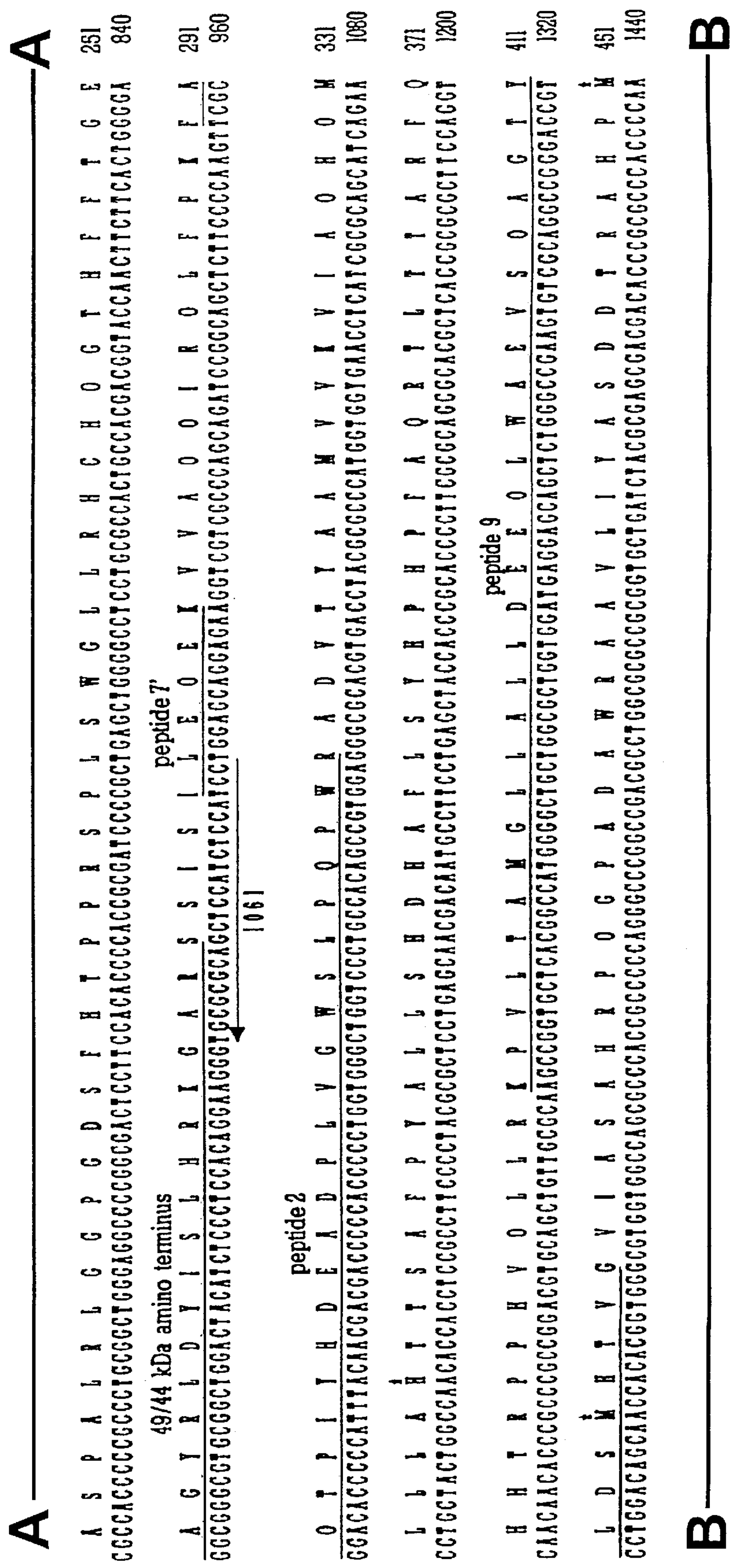

It is certified that error appears in the above-identified patent and that said Letters Patent is hereby corrected as shown below:

Column 7, line 33, delete "FIGURE 2 (SEQ ID NO:4) is a representation of" and insert therefor -- FIGURES 2a through 2c (SEQ ID NO: 4) when joined at the match line form -- .

Column 7, line 60, delete "FIGURE 4 (SEQ ID NO: 6) shows" and insert therefor

-- FIGURES 4a through 4d (SEQ ID NOs: 6-7) when joined at the match line show -- .

Signed and Sealed this

Twenty-ninth Day of May, 2001

Attest:

Nicholas P. Godici

NICHOLAS P. GODICI

*Attesting Officer*

*Acting Director of the United States Patent and Trademark Office*